United States Patent [19]  
Holmes

[11] 4,110,465  
[45] Aug. 29, 1978

[54] 7-AMINO AND 7-ALKANOYLAMINO 2-OXO-3-PHENYLINDOLINES

[75] Inventor: Richard E. Holmes, Indianapolis, Ind.

[73] Assignee: Eli Lilly and Company, Indianapolis, Ind.

[21] Appl. No.: 854,879

[22] Filed: Nov. 25, 1977

[51] Int. Cl.$^2$ .................... A61K 31/40; C07D 209/34
[52] U.S. Cl. ................. 424/274; 260/325 R; 260/558 P
[58] Field of Search .................... 260/325 R; 424/274

[56] References Cited  
PUBLICATIONS

Mullock et al., J. Chem. Soc., 1970, pp. 829–833.

Primary Examiner—Alton D. Rollins  
Attorney, Agent, or Firm—James L. Rowe; Arthur R. Whale

[57] ABSTRACT

7-Amino and 7-alkanoylamino-2-oxo-3-phenylindolines, useful as anti-inflammatory and anti-thrombotic agents.

6 Claims, No Drawings

7-AMINO AND 7-ALKANOYLAMINO 2-OXO-3-PHENYLINDOLINES

BACKGROUND OF THE INVENTION

Amino-substituted indolin-2(3H)-ones have been prepared by the polyphosphoric acid catalyzed cyclization of mandel (o- and p-amino-substituted)anilides. 5- and 7-Pyrrolidino, piperidino, homopiperidino, N-methyl piperazino and morpholino indolin-2(3H)-ones were prepared, according to Mullock et al., J. Chem. Soc., 1970, 829.

SUMMARY OF THE INVENTION

This invention provides compounds of the formula

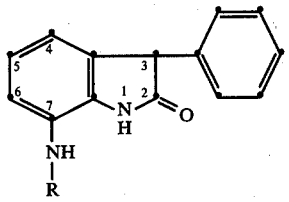

wherein R is H or $(C_1-C_3)$alkyl-CO.

In the above formula, the term $(C_1-C_3)$alkyl-CO represents an alkanoyl radical of 2-4 carbon atoms including acetyl, propionyl, butyryl and isobutyryl. Compounds in which R is $(C_1-C_3)$alkyl-CO can be named as 7-alkanoylaminoindolines; i.e., 7-acetylamino-2-oxo-3-phenylindoline, but I prefer to name them as substituted alkanoyl amides; i.e., as N-(2-oxo-3-phenyl-7-indolinyl)acetamide (or propionamide etc.). Illustrative compounds thus include:

N-(2-oxo-3-phenyl-7-indolinyl)propionamide;
N-(2-oxo-3-phenyl-7-indolinyl)n-butyramide;
N-(2-oxo-3-phenyl-7-indolinyl)isobutyramide.

The compounds of this invention are prepared according to the following procedure; o-nitroaniline is acylated with α-chlorophenylacetyl chloride or α-chlorophenylacetic anhydride in the presence of a base such as triethylamine or pyridine. The reaction is carried out in an inert solvent, preferably an aromatic hydrocarbon solvent such as xylene. α-Chloro-α-phenyl-2-nitroacetanilide thus prepared is cyclized with polyphosphoric acid to yield 2-oxo-3-phenyl-7-nitroindole. Reduction of the nitro group as with a metal catalyst at low hydrogen pressure yields 2-oxo-3-phenyl-7-aminoindole, one of the compounds represented by the above formula. Acylation of this compound with a lower alkanoyl halide or anhydride yields an N-(2-oxo-3-phenyl-7-indolinyl)alkanoyl amide, compounds also represented by the above formula. The above procedure is more specifically illustrated by the following example.

EXAMPLE 1

Preparation of α-Chloro-α-phenyl-2-nitroacetanilide

A solution of 35 g. of o-nitroaniline and 26 g. of triethyl amine in 600 ml. of xylene was heated to reflux. A solution of 50 g. of α-chlorophenylacetyl chloride in 200 ml. of xylene was added and the resulting mixture heated to reflux temperature for 18 hours. The reaction mixture was filtered and the filtrate concentrated in vacuo to a residue comprising α-chloro-α-phenyl-2-nitroacetanilide formed in the above reaction. Recrystallization of the residue from methanol yielded material melting 80°-82° C.; yield = 55 g.

Analysis calc.: C, 57.84; H, 3.81; N, 9.64; Cl, 12.20; Found: C, 57.84; H, 3.90; N, 9.63; Cl, 12.29.
Molecular weight calculated 290.706; molecular weight by mass spectrum 290.

EXAMPLE 2

Preparation of 2-Oxo-3-phenyl-7-nitroindole

A mixture of 10 g. of α-chloro-α-phenyl-2-nitroacetanilide and 300 g. of polyphosphoric acid was heated at 90° C. for 18 hours after which time the reaction mixture was poured into 2500 ml. of water. The solids which precipitated were separated by filtration. The filter cake was dissolved in 700 ml. of ethyl acetate. The ethyl acetate solution was washed twice with 200 ml. of saturated aqueous sodium bicarbonate and twice with 200 ml. of water. The ethyl acetate layer was then dried and the solvent removed by evaporation in vacuo. The residue, consisting of 2-oxo-3-phenyl-7-nitroindole formed in the above reaction, was recrystallized first from ethanol and then from ether. The compound melted 175°-177° C.; yield = 1.3 g.

Analysis calc.: C, 66.14; H, 3.96; N, 11.02; O, 18.88; Found: C, 66.23; H, 4.10; N, 10.81; O, 18.61.
Molecular weight calculated 254.245; molecular weight by mass spectrum 254.

EXAMPLE 3

Preparation of 2-oxo-3-phenyl-7-aminoindole

Two and one half grams of 2-oxo-3-phenyl-7-nitroindole were dissolved in 200 ml. of THF (tetrahydrofuran). Two grams of 5% palladium-on-carbon were added and the mixture placed in a low pressure hydrogenation apparatus at 60 psi of hydrogen. After 18 hours, the theoretical amount of hydrogen had been absorbed. The hydrogenation mixture was filtered to remove the catalyst and the filtrate was evaporated to dryness in vacuo. The residue containing the 2-oxo-3-phenyl-7-aminoindole formed in the above hydrogenation melted at 226°-30° C. after recrystallization from methanol; yield = 1.5 g.

Analysis calc.: C, 74.98; H, 5.39; N, 12.49; O, 7.13; Found: C, 74.08; H, 5.31; N, 11.88; O, 7.97.
Molecular weight calculated 224.263; molecular weight by mass spectrum 224.

EXAMPLE 4

Preparation of N-(2-oxo-3-phenyl-7-indolinyl)acetamide

Ten milliliters of acetic anhydride were added to a solution of 2-oxo-3-phenyl-7-aminoindole (0.7 g.) in 40 ml. of pyridine. The reaction mixture was stirred at ambient temperature for 18 hours. Ten milliliters of water were then added and the solvent removed in vacuo. The residue was treated with 100 ml. of 1 N aqueous hydrochloric acid. The resulting solids were separated by filtration and the filter cake washed with water. Recrystallization of the filtered material from methanol yielded N-(2-oxo-3-phenyl-7-indolinyl)acetamide formed in the above reaction melting at 258°-62° C.; yield = 490 mg.

Analysis calc.: C, 72.17; H, 5.30; N, 10.52; O, 12.02; Found: C, 71.96; H, 5.35; N, 10.35; O, 11.77.
Molecular weight calculated 266.300; molecular weight by mass spectrum 266.

The compounds of this invention are anti-inflammatory and anti-thrombotic agents. Their anti-inflammatory activity can be demonstrated by their ability to block the erythema produced by an ultra-violet light source on guinea pig skin according to the method of Windner, et al, Arch. Int. Pharmacodyn, 116, 261 (1958). In this procedure, albino guinea pigs weighing 225-300 gms. are shaved on the back and chemically depilated 18 to 20 hours before initiation of the test procedures. Animals in groups of 4 are given predetermined dosages of the drug under test with one group being maintained as a control group. The drug is administered by the oral route as a suspension in 1 percent aqueous sodium carboxymethylcellulose. The control animals receive only the suspending medium. After having being given the drug or suspension medium only, each group of animals is exposed to a high-intensity ultra-violet light for a predetermined period of time, the ultra-violet light being placed in contact with the depilated skin area on the animals' back. A gummed paper reinforcement is affixed to the lamp lens to provide an unexposed area of contrast for grading the light-produced erythema.

Beginning one hour after exposure and thereafter an half-hour intervals for another 1.5 hours, a trained observer grades erythema using an arbitrary scoring system based upon the degree of contrast and redness formed. The scores are weighted by factors of 4,3,2, and 1 at the 0.0, 1.5, 2.0 and 2.5 hour scoring times respectively because anti-inflammatory agents are usually less effective with the passage of time. The following scoring system is used:

| Score | Appearance of Exposed Area |
|---|---|
| 0 | No redness and no contrast |
| 1 | Slight redness with a faint reinforcement outline |
| 2 | Slight to moderate redness with a distinct outline |
| 3 | Marked redness with a distinct circular outline |

Total scores from each treatment group of four guinea pigs are compared to the control treatment, and the percent inhibition calculated as follows:

$$100 \times \frac{\left(\text{Control Score} - \text{Treatment Score}\right)}{\text{Control Score}} = \text{Percent Inhibition}$$

If desired, a dose-response graph can be obtained by plotting dose versus percent inhibition, each point representing the average of one treatment group of four guinea pigs. The dose ($ED_{50}$) in mg/kg which produced a 50 percent inhibition of the erythemic response for the particular compound tested can then be obtained, either directly or by extrapolation. Table I below summarizes the results obtained from testing representative compounds of the invention by the foregoing method.

Certain of the compounds of this invention are also platelet aggregation inhibitors and the results of testing for this activity are also included in Table I. The platelet aggregation test used involves the effect of a drug upon collagen-induced platelet aggregation using the method of Hermann et al., Proc. Soc. Exp. Biol. Med. 136, 548 (1972). According to this procedure, 300-400 g. guinea pigs are used and the compound is administered by the oral route in 2 doses, at time zero and again 2 hours later, at a series of graded dose levels to groups of 4 pigs each. One group is maintained as a control group. Blood is removed by heart puncture 60 minutes after the last dose, and a platelet-rich plasma prepared therefrom. A stock collagen solution is prepared by solubilizing bovine Achilles tendon with acetic acid. The stock solution contains 0.25 percent collagen, has a pH of 2.8 and is kept under refrigeration. Prior to use, 0.4 ml. of 1M aqueous sodium hydroxide is added to a 1 ml. aliquot of the stock solution, followed by further dilutions with saline (1:2, 1:4, 1:8, 1:16, 1:32, etc.) A standard collagen challenge was used, 0.05 ml. of 1:45 dilution, to induce platelet aggregation and the aggregation response of the drugged guinea pigs was compared to that of the controls to determine inhibition of aggregation. The lowest active dose in mg./kg. × 2 was then determined, "active" being defined as giving about 50% inhibition of collagen-induced aggregation. (Activity was determined by computor printout with significance at the 95 percent confidence level being attained at about the 50 percent inhibition level). These lowest effective dose levels are also given in Table 1 which follows. In Table 1, column 1 gives the name of the compound, column 2, the $ED_{50}$ for erythema blocking calculated as set forth above and column 3, the lowest active dose in the platelet aggregation test.

Table 1

| Name of Compound | $ED_{50}$ in mg/kg | P.A. mg/kg × 2 |
|---|---|---|
| 2-oxo-3-phenyl-7-aminoindoline | 10.2 | 100 |
| N-(2-oxo-3-phenyl-7-indolinyl)-acetamide | 20 | 3.12 |

As anti-inflammatory agents, the compounds of this invention can be administered to mammals suffering from inflammation, either orally or parenterally, and in the case of inflammation of body surface, by topical application.

The amount of the compound or compounds employed is not critical so long as an effective, anti-inflammatory amount is used. In general, anti-inflammatory activity is exhibited at doses of from 1.0 to 50 or more mg./kg. of animal body weight.

In carrying out the anti-inflammatory methods of the present invention, it is generally preferred to employ a composition comprising the active agent and one or more adjuvants suited to the particular route of administration. Compositions for oral administration may be either solid, e.g, capsules, tablets, pills, powders, etc., or liquid, e.g., emulsions, solutions, suspensions, syrups, elixirs, etc. In the case of solid formulations, suitable adjuvants include inert substances such as sucrose, lactose, and starch. In the case of liquid formulations, suitable adjuvants include water, mineral oil, etc. Either solid or liquid formulation can include lubricating agents, wetting agents, emulsifying and suspending agents, preserving agents, sweetening agents, flavoring agents, or perfuming agents.

In the instance of parenteral administration, the compounds of the present invention are formulated in a suitable sterile, injectable liquid.

Formulations suitable for topical administration include lotions, ointments, creams, spray, etc. Conventional adjuvants are employed.

In general, oral administration is preferred. Accordingly, a preferred formulation is a pharmaceutical preparation in dosage unit form adapted for administration to obtain an anti-inflammatory effect, comprising, per dosage unit, an effective non-toxic amount within the range from about 10 to about 500 milligrams of one or more of the compounds or this invention. For many applications, the above preparation may suitably contain only a lesser amount of active agent, such as from about 5 to about 100 milligrams.

In employing the compounds of this invention which have anti-thrombotic activity in the treatment of vascular thrombosis, it should be emphasized that such treatment is customarily prophlyactic in nature. Thus, there is administered to an individual an amount of drug based upon his need for such administration. In general, an individual will require treatment with an anti-thrombotic agent under either of two situations: (1) the individual already has suffered overt manifestations of a thromboembolic disease, or (2) the individual has an identifiable risk of contracting a thromboembolic disease but has not yet shown any overt manifestations of such disease. In either case, the prophylactic treatment of the individual with an anti-thrombotic agent is intended to prevent further thromboembolic disease in the individual or, at least, to minimize the effects of such disease. For prophylaxis of incipient or overt thromboembolic disease, the oral route of administration is preferred, utilizing the oral dosage forms set forth above.

We claim:

1. A compound of the formula

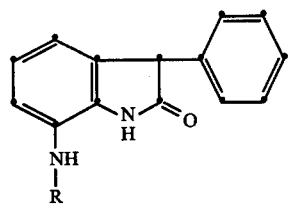

wherein R is H or $(C_1-C_3)$alkyl-CO.

2. A compound according to claim 1 in which R is H, said compound being 2-oxo-3-phenyl-7-aminoindoline.

3. A compound according to claim 1 in which R is $CH_3$-CO, said compound being N-(2-oxo-3-phenyl-7-indolinyl)acetamide.

4. A method of treating inflammation in a warm-blooded mammal which comprises administering to a warm-blooded mammal suffering from an inflammatory process an anti-inflammatorially effective amount of a compound according to claim 1.

5. A method of treating vascular thrombosis in mammals which comprises administering to a mammal in need of such treatment an amount of a compound according to claim 1 effective for treating vascular thrombosis.

6. A therapeutic composition in unit dosage form adapted for administration to achieve an anti-inflammatory effect, comprising, per unit dosage from 10–500 mg. of a compound according to claim 1 and a pharmaceutical diluent.

* * * * *